US00PP36233P2

(12) United States Plant Patent
Rosas et al.

(10) Patent No.: US PP36,233 P2
(45) Date of Patent: Nov. 5, 2024

(54) STRAWBERRY PLANT VARIETY NAMED 'Plared 19106'

(50) Latin Name: ***Fragaria* x *ananassa***
Varietal Denomination: Plared 19106

(71) Applicant: Plantas de Navarra S.A., Valtierra (ES)

(72) Inventors: Manuel Rosas, Anderson, CA (US); Pedro Dominguez, Anderson, CA (US)

(73) Assignee: Plantas De Navarra S.A., Valtierra (ES)

( * ) Notice: Subject to any disclaimer, the term of this patent is extended or adjusted under 35 U.S.C. 154(b) by 0 days.

(21) Appl. No.: 18/445,834

(22) Filed: Feb. 23, 2024

(51) Int. Cl.
*A01H 5/08* (2018.01)
*A01H 6/74* (2018.01)

(52) U.S. Cl.
USPC ..... Plt./209

(58) Field of Classification Search
USPC ..... Plt./208, 209
See application file for complete search history.

(56) References Cited

U.S. PATENT DOCUMENTS

PP20,552 P3 12/2009 Shaw et al.
PP31,259 P3 12/2019 Pierron-Darbonne

*Primary Examiner* — Susan McCormick Ewoldt
(74) *Attorney, Agent, or Firm* — Hunt IP Law

(57) ABSTRACT

The new and distinct variety of strawberry plant variety 'Plared 19106' is provided. The variety can be distinguished by its outstanding features of an upright plant architecture and darker red fruit, increased production, and firmer long oblong fruit.

5 Drawing Sheets

Botanical classification: a. Genus-*Fragaria*. b. Species-x *ananassa*.

Variety denomination: The new strawberry plant claimed is of the variety denominated 'Plared 19106'.

BACKGROUND OF THE INVENTION

Field of the Invention

The present invention relates to a new and distinct annual variety of strawberry plant, which has been given the variety denomination of 'Plared 19106'.

Background of the Related Art

Cultivated strawberry is a hybrid species of the genus *Fragaria* that is grown worldwide for its fruit. Modern strawberry was first bred in Brittany, France, in the 18$^{th}$ century by crossing *Fragaria virginiana* with *Fragaria chiloensis*. Strawberry fruit is an aggregate accessory fruit, with the fleshy part of the fruit being derived from the receptacle that holds the ovaries.

Strawberry varieties vary widely in color, size, shape, flavor, season of ripening, degree of fertility, and susceptibility to disease. Certain varieties vary in foliage, and some vary in the relative development of their reproductive organs. Typically, strawberry flowers appear hermaphroditic in structure, but function as either male or female. Generally, commercial production of strawberry plants involves propagation from runners and distribution as either plugs or bare root plants. Cultivation is either perennial or annual plasticulture. During the off season, strawberries can also be produced in greenhouses.

Strawberry fruit is widely appreciated for its characteristic bright red color, aroma, juicy texture, and sweetness. Strawberry fruit is a popular fruit that is generally consumed either fresh or in prepared foods, such as preserves and baked goods.

Strawberries are an important and valuable fruit crop. Accordingly, there is a need for new varieties of strawberry plants. In particular, there is a need for improved varieties of strawberry plant that are stable, high yielding, and agronomically sound.

SUMMARY OF THE INVENTION

The present invention relates to a new and distinct annual variety of strawberry, which has been given the variety denomination of 'Plared 19106'. Its market class is that of summer planted variety. 'Plared 19106' is intended for use as a frigo plant to be planted in the summer and produce fresh fruit in the fall and beyond.

The new strawberry variety is a selection resulting from a sexual cross of strawberry plants at Watsonville, California in 2018, involving a seed parent known as 'Plared 0822' (U.S. Plant Pat. No. 31,259) and a pollen parent known as '16-69' (unpatented).

The selection was subsequently evaluated for four years in Watsonville, California.

Asexual reproduction of the new variety by cutting propagation since 2019 Watsonville, California has demonstrated that the new variety reproduces true to type with all of the morphological characteristics, as herein described, firmly fixed and retained through successive generations of such asexual propagation.

Selection criteria was based on the needs the California fresh fruit market and was optimized for the summer planting for targeted production ideotype.

Plants of the new variety differ from plants of the seed parent 'Plared 0822', for example, in terms of vigor, 'Plared 19106' is more vigorous than 'Plared 0822', and the fruit color is darker in the case of 'Plared 19106'. Plants of the new variety differ from plants of the pollen parent '16-69', for example, fruits of 'Plared 19106' presents an oblong shape and '16-69' presents a conical shape. Further, the color of the fruit is darker in 'Plared 19106' than for the parental '16-69'.

Plants of the new variety differ from the known reference variety 'Portola' (U.S. Plant Pat. No. 20,552) as shown in Table 1.

TABLE 1

Comparison of 'Plared 19106' and 'Portola'

| Characteristic | 'Plared 19106' | 'Portola' |
|---|---|---|
| Density of Foliage | Medium | Strong |
| Fruit Shape | Oblong | Conical |
| Fruit Color | sRGB 180, 0, 7 | sRGB 246, 71, 65 |

BRIEF DESCRIPTION OF THE DRAWINGS

The accompanying photographic illustrations show the typical appearance of the new variety 'Plared 19106'. The colors are as nearly true as is reasonably possible in a color representation of this type. Colors in the photographs may differ slightly from the color values cited in the detailed botanical description which accurately describes the colors of the new plant.

DETAILED BOTANICAL DESCRIPTION

Figure 1:
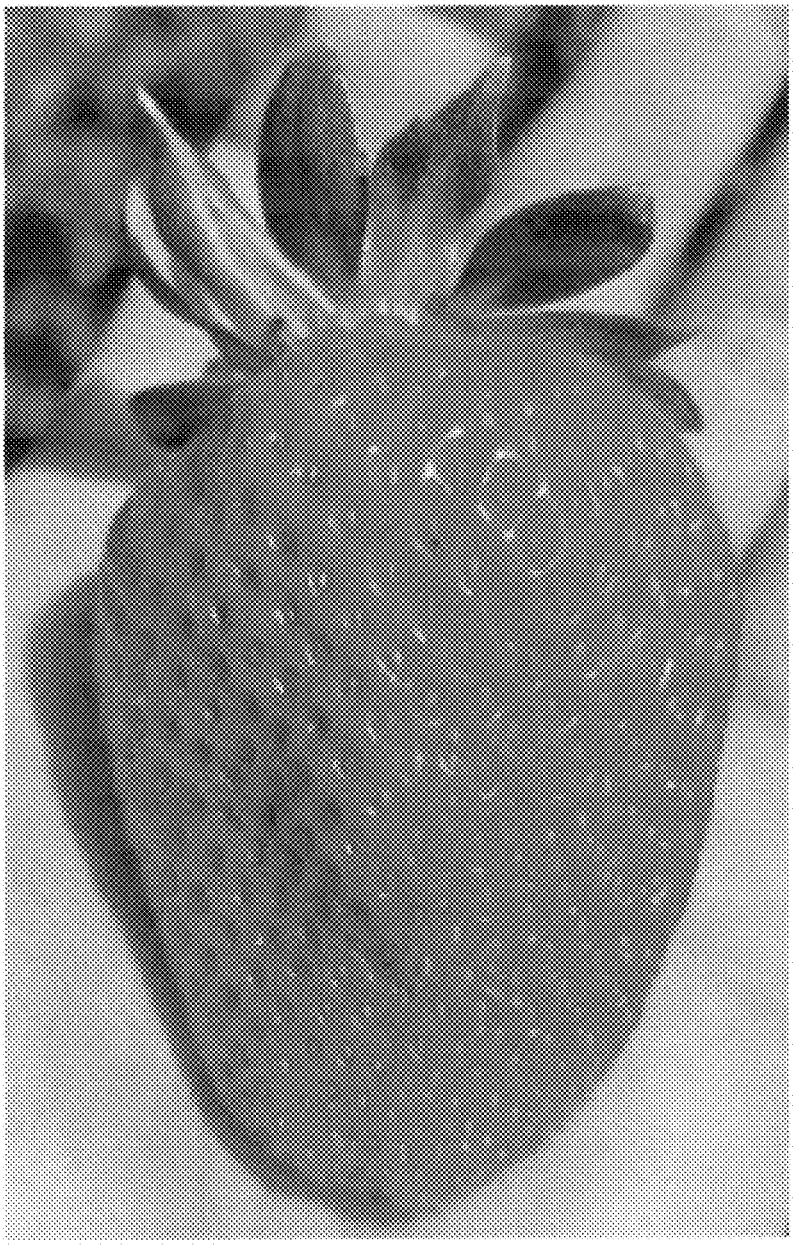
FIG. 1 is a photograph of the new variety 'Plared 19106', demonstrating its dark red elongated fruit.
Figure 2:
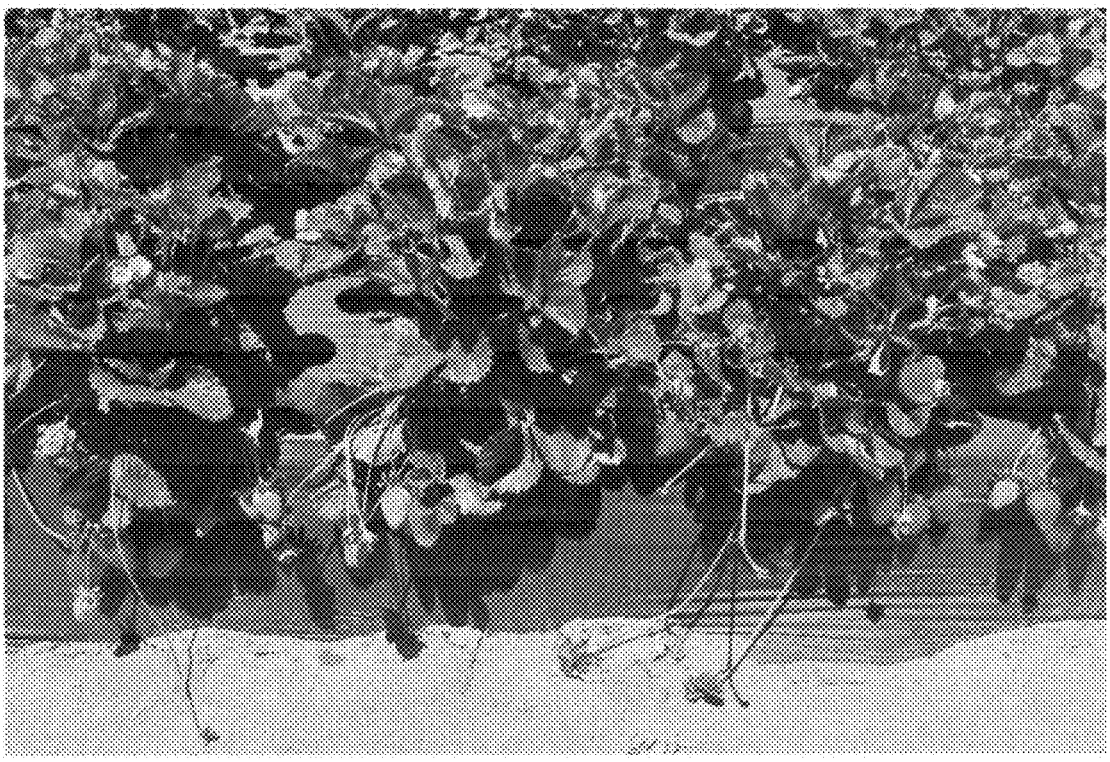
FIG. 2 is a photograph of the new variety 'Plared 19106', demonstrating its upright architecture and summer planting adaptation. This photo was taken on Sep. 7, 2022, 82 days after planting using frigo plants.
Figure 3:
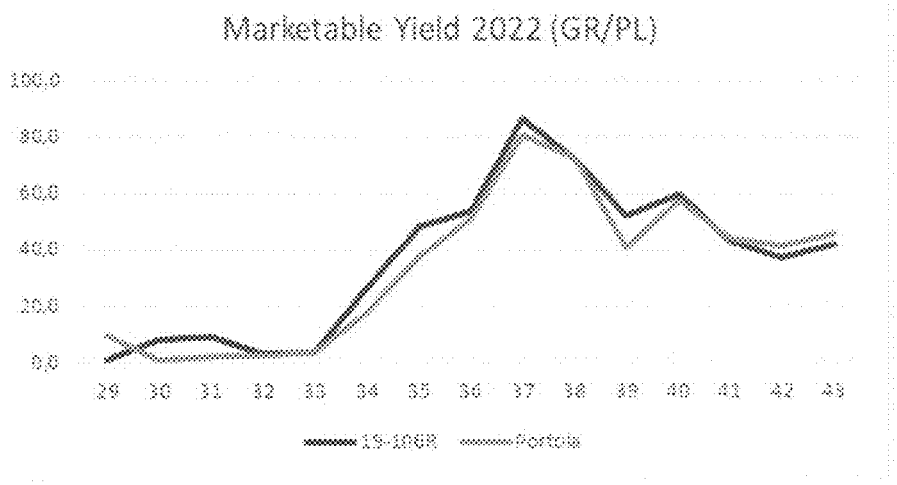
FIG. 3 is a bar graph of marketable yield over three summer planting seasons of new variety 'Plared 19106' and industry reference 'Portola'.
Figure 4:
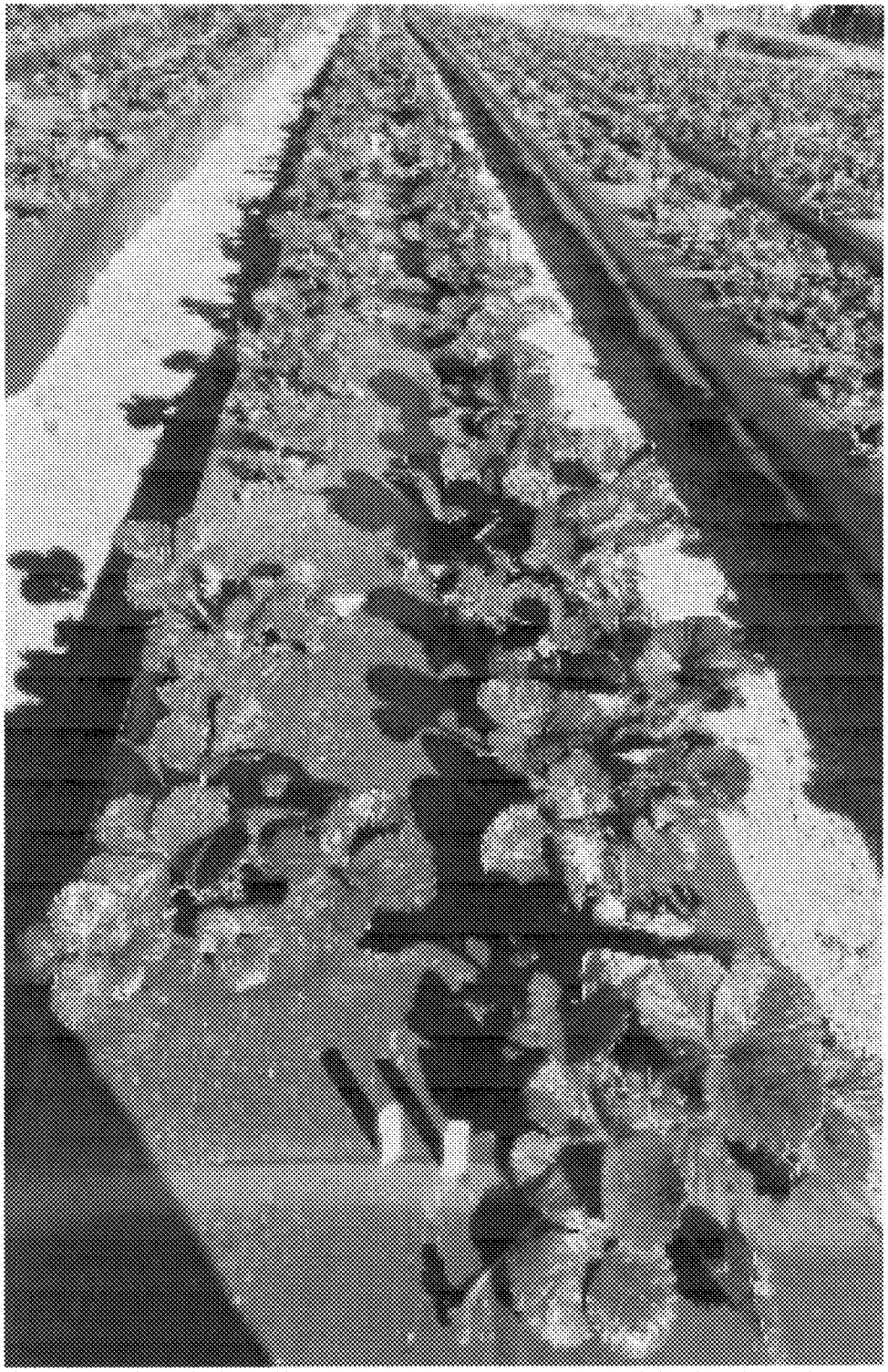
FIG. 4 is a photograph of the new variety 'Plared 19106'.
Figure 5:
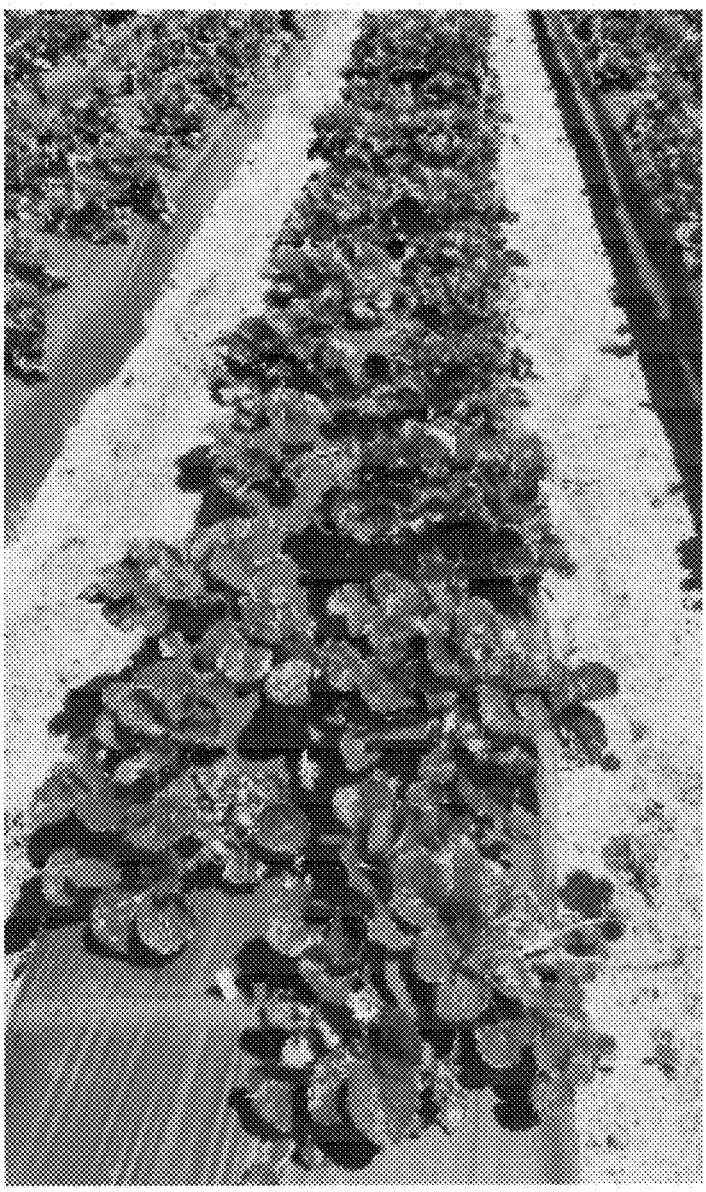
FIG. 5 is a photograph of the new variety 'Plared 19106'.

The following detailed description sets forth the distinctive characteristics of 'Plared 19106'. The datum which defines these characteristics was collected from asexual reproductions of the original selection. Dimensions, sizes, colors, and other characteristics are approximations and averages set forth as accurately as possible. The plant history was taken on plants approximately 175 Days, and the descriptions relate to plants grown in Watsonville, California. Color notations are in reference to the standard RGB (sRGB) color space.

*Classification*.—a. Family — Rosaceae. b. Botanical — *Fragaria*. c. Common Name — Strawberry. d. Variety Name — 'Plared 19106'.

*Parentage*.—a. Female Parent — 'Plared 0822' (U.S. Plant Pat. No. 31,259). b. Male Parent — '16-69' (unpatented).

PLANT

*General*.—a. Height — 20 cm. b. Diameter — 25 cm. c. Number of crowns per plant — 6. d. Growth habit — Upright. e. Density of foliage — Medium Density. f. Vigor — Medium. g. Stolon i. Average number of daughter plants per sq. ft. — 8.2. ii. Diameter at bract — 0.95 cm. iii. Anthocyanin coloration — Dark red (sRGB 155, 68, 54). iv. Anthocyanin color — Dark red (sRGB 160, 72, 77). v. Stolon color — Light Green (sRGB 217, 233, 144). vi. Density of pubescence on the stolon — Medium. h. Hardiness zone — 16° C.-27° C. Hardiness zone 13.

LEAVES

*General*.—a. Number of leaflets — 3. b. Color of upper surface — Dark Green (sRGB 47, 95, 49). c. Color of lower surface — Light Green (sRGB 107, 161, 152). d. Leaf blistering — Strong. e. Leaf glossiness — Strong. f. Variegation — Absent. g. Terminal leaflet. i. Length — 5.6 cm. ii. Width — 6.1 cm. iii. Length/width ratio — 0.9. iv. Number of teeth/terminal leaflet — 20. v. Shape of base — Flat. vi. Margin — Serrate to Crenate. vii. Shape in cross section — Concave to Straight. viii. Shape of apex — Rounded. a. Petiole. i. Length — 19 cm. ii. Diameter — 0.3 cm. iii. Attitude of hairs — Downwards. iv. Bract frequency (number present on each petiole) — N/A. v. Color — Light Green (sRGB 178, 219, 131). b. Petiolule. i. Length — Long. 9-11 mm. ii. Color — Light Green (sRGB 152, 195, 133). c. Stipule. i. Length — 2.5 cm. ii. Width — 1.3 cm. iii. Anthocyanin coloration — Present. iv. Anthocyanin color — (sRGB 240, 46, 53). v. Stipule color — Translucent Green (sRGB 195, 230, 203).

INFLORESCENCE

*General*.—a. Position in relation to foliage — Above. b. Pedicel. i. Attitude of hairs — Upwards. ii. Length — 30 cm. iii. Diameter — 0.4 cm. iv. Color — Light Green (sRGB 174, 204, 25). c. Flower. i. Arrangement of petals — Overlapping. ii. Stamen — Present. iii. Anther color (if stamen is present) — Dark Yellow (sRGB 205, 169, 95). iv. Number of flowers per inflorescence — 2-6. v. Mean diameter of individual flower —25-30 mm. d. Petal. i. Length/width ratio — Equal. ii. Typical and observed petal number — 6-8. iii. Color of upper side — White (sRGB 255, 255, 255). iv. Color of lower side — White (sRGB 255, 255, 255). e. Calyx. i. Color — Green (sRGB 0, 51, 0). ii. Mean diameter — 22 mm. f. Sepal. i. Color of surface — Dark green (sRGB 66, 101, 27). ii. Color of lower surface — Medium Green (sRGB 139, 165, 64). iii. Attitude of sepals — Upward to away from berry.

FRUIT

*General*.—a. Fruit weight — 31 grams (2022 season average). b. Shape — Elongated conical. c. Differences in shape between primary and secondary fruit — Moderate. d. Glossiness — Medium. e. Firmness — Strong Firmness. f. Color — Dark Red (sRGB 180, 0, 7). g. Evenness of fruit color — Even. h. Position of achenes — Above with Surface. i. Number of fruit per truss — 2-4. j. Position of calyx attachment — Raised. k. Color of flesh (excluding core) — Dark Red (sRGB 180, 0, 7). l. Color of core — Red with White (sRGB 223, 88, 56). m. Sugar content (as soluble solids in degrees brix) — 8.8%(2022 season average). n. Production. i. Flowering interval — Beginning approximately 2 weeks of planting in summer with frigo plants, continuous flowering thereafter. ii. Harvest interval — Beginning approximately 6 weeks after planting in summer with frigo plants, continuous harvest thereafter. iii. Type of bearing — Day-Neutral. iv. Productivity — Three-year average of 850 grams per plant produced within five months of summer planting using frigo plants (e.g., planting in early June and harvesting through October). o. Width of band without achenes — Narrow or absent. p. Adherence to calyx — Strong. q. Cavity size — Absent. r. Storage life — Very good storage life. s. Market use — The fruits of Plared 19106 will be used for the commercial fresh fruit market, mainly for the summer and fall production.

The invention claimed is:

1. A new and distinct variety of strawberry plant named 'Plared 19106', as illustrated and described herein.

* * * * *